(12) United States Patent
Kim

(10) Patent No.: US 8,998,615 B2
(45) Date of Patent: Apr. 7, 2015

(54) METHOD AND APPARATUS FOR PREPARING DENTURE

(71) Applicant: Dentca, Inc., Los Angeles, CA (US)

(72) Inventor: Tae Hyung Kim, La Canada, CA (US)

(73) Assignee: Dentca, Inc., Los Angeles, CA (US)

( * ) Notice: Subject to any disclaimer, the term of this patent is extended or adjusted under 35 U.S.C. 154(b) by 0 days.

(21) Appl. No.: 14/031,352

(22) Filed: Sep. 19, 2013

(65) Prior Publication Data

US 2014/0017634 A1    Jan. 16, 2014

Related U.S. Application Data

(63) Continuation-in-part of application No. 13/598,413, filed on Aug. 29, 2012, now Pat. No. 8,899,983, which is a continuation of application No. 12/782,663, filed on May 18, 2010, now Pat. No. 8,277,216.

(60) Provisional application No. 61/179,698, filed on May 19, 2009.

(51) Int. Cl.
*A61C 9/00* (2006.01)
*A61C 13/00* (2006.01)
*A61C 19/05* (2006.01)

(52) U.S. Cl.
CPC ........... *A61C 9/0006* (2013.01); *A61C 13/0004* (2013.01); *A61C 19/05* (2013.01)

(58) Field of Classification Search
CPC .................................................... A61C 9/0006
USPC ............... 433/34–37, 41–48, 199.1, 214, 215
See application file for complete search history.

(56) References Cited

U.S. PATENT DOCUMENTS 2,011,860 A * 8/1935 Kalvin ............................ 433/48
3,626,594 A   12/1971 Zinner et al.
(Continued)

FOREIGN PATENT DOCUMENTS

JP    33-17491      10/1958
JP    11-318956     11/1999
(Continued)

OTHER PUBLICATIONS

Korean Intellectual Property Office Application Serial No. 10-2011-7026028, Notice of Allowance dated Nov. 19, 2013, 2 pages.
(Continued)

*Primary Examiner* — Ralph Lewis
(74) *Attorney, Agent, or Firm* — Lee, Hong, Degerman, Kang & Waimey

(57) ABSTRACT

In a method of obtaining a gum impression of a patient's mouth and measuring jaw relations, a dental impression tray assembly including a lower tray and an upper tray to fabricate a denture, is used. The lower tray includes a first piece and a pair of second pieces and the upper tray includes a third piece and fourth piece. The method includes inserting the lower tray loaded with an impression material into the mouth to take an impression; taking out the lower tray from the mouth and cutting the impression material along a borderline between the first piece and the pair of second pieces; separating the first piece from the pair of second pieces; attaching an intra-oral tracer to the first piece and inserting the first piece, to which the intra-oral tracer is attached, and the third piece into the mouth to measure the jaw relations.

16 Claims, 6 Drawing Sheets

(56) References Cited

U.S. PATENT DOCUMENTS

| | | |
|---|---|---|
| 3,890,711 A | 6/1975 | Burns |
| 4,145,812 A | 3/1979 | Johnson et al. |
| 4,445,854 A | 5/1984 | Bekey et al. |
| 4,543,062 A | 9/1985 | Lee |
| 4,657,509 A | 4/1987 | Morris |
| 4,789,334 A | 12/1988 | Wedenig et al. |
| 5,186,624 A | 2/1993 | Gottsleben |
| 6,196,840 B1 | 3/2001 | Zentz et al. |
| 2003/0180681 A1 | 9/2003 | Kwon et al. |
| 2007/0190492 A1 | 8/2007 | Schmitt |
| 2008/0254406 A1 | 10/2008 | Wagner |
| 2010/0297572 A1* | 11/2010 | Kim ................... 433/71 |

FOREIGN PATENT DOCUMENTS

| | | |
|---|---|---|
| JP | 2006-192223 | 7/2006 |
| JP | 2009-517144 | 4/2009 |
| KR | 10-2009-0036643 | 4/2009 |
| RU | 2306113 | 1/2007 |
| SU | 53029 | 4/1938 |
| WO | 02-00134 | 1/2002 |
| WO | 2008/083857 | 7/2008 |

OTHER PUBLICATIONS

United States Patent and Trademark Office U.S. Appl. No. 12/782,663, Advisory Action dated Jun. 6, 2012, 3 pages.

The State Intellectual Property Office of the People's Republic of China Application Serial No. 201080021927.3, Office Action dated Jan. 21, 2014 7 pages.

Japan Patent Office Application Serial No. 2012-511977, Office Action dated Feb. 6, 2014, 6 pages.

Russian Federation Federal Service for Intellectual Property, Patents and Trademarks Application Serial No. 2011151435/14, Office Action dated Nov. 18, 2014, 5 pages.

* cited by examiner

METHOD AND APPARATUS FOR PREPARING DENTURE

CROSS REFERENCE TO RELATED APPLICATIONS

This is a continuation-in-part of U.S. patent application Ser. No. 13/598,413, filed on Aug. 29, 2012, which is a continuation of U.S. patent application Ser. No. 12/782,663, filed on May 18, 2010, now U.S. Pat. No. 8,277,216, which pursuant to 35 U.S.C. §119(e) claims the benefit of U.S. Provisional Application No. 61/179,698, filed on May 19, 2009, the contents of which are all hereby incorporated by reference herein in their entirety.

FIELD OF THE INVENTION

The present disclosure relates generally to dentures, and more particularly to a simplified method and apparatus for fabricating dentures. In particular, the present invention is directed to reducing a number of visits required for fabrication of a denture without compromising the quality of the denture by using the inventive method and apparatus. Thus, the inventive method and apparatus is capable of greatly reducing the manufacturing time, human errors, and the cost of making the final dentures, enhancing the final denture quality due to three-dimensional (3D) modeling and production techniques.

DESCRIPTION OF THE RELATED ART

Complete dentures are constructed to replace missing teeth for patients who are fully edentulous. Fabrication of a set of complete dentures is a challenging task for any dentist. Complete dentures should be comfortable when inserted into the mouth of a patient. Therefore, impressions of edentulous patients must be accurate, duplicating all the details of the oral tissues. Imperfection in the impression affects the fit of the dentures, and thus, may cause serious effects when wearing the dentures.

Dentures are conventionally constructed and fitted by dentists with the assistance of dental technicians using a flask investment technique. This complex process requires measurements of masticatory function, impressions of the gum and surrounding tissues of the affected area, study models and working models, and a series of back and forth steps between the dentist and the dental technician to manufacture the denture. The entire process of constructing dentures using conventional methods and devices requires a number of appointments between the dentist and the patient, and involves a significant amount of time and skill.

Generally, a patient must make a plurality of visits to a dentist to make a set of dentures. Such visits are necessary in order for a dentist to take an impression of the patient's gums, as well as a bite registration of the patient's jaw position and vertical dimension.

For example, during a first visit, a dentist examines a patient and takes a preliminary alginate impression of the patient using stock trays. After the preliminary alginate impression is taken on the impression material, the impression tray is delivered to a laboratory. In the laboratory, plaster is poured onto the preliminary alginate impression to form accurate models of the shape of the edentulous ridges. The preliminary alginate impression is used to make custom fitting impression trays for a final impression.

During a second visit, the dentist checks and adjusts custom fitting impression trays as necessary and takes the final impression. Afterwards, in the laboratory, a master model is created and a base plate is fabricated based on the final impression received from the dentist. Then, a bite registration rim or block, usually made of wax, is fabricated from the master gum mold. The master gum mold, with the bite registration rim attached thereto, is sent back to the dentist.

During a third visit, the bite registration rim is inserted into the mouth of the patient, and adjusted inside the mouth to determine maxilla-mandibular relations and to take a bite registration. Further, artificial teeth to be used for the denture are selected by the dentist and the patient. The adjusted bite registration rim is sent back to the laboratory to fabricate a wax try-in. The laboratory returns the wax try-in with the actual final teeth lined up along the outer edge of the wax rim. The wax try-in looks similar to a real denture except that the base fits loosely on the gums and the teeth are embedded in wax instead of plastic.

During a fourth visit, the dentist examines how the wax try-in looks and works in the patient, checking occlusal and vertical dimension. If adjustments are necessary, the wax try-in can be sent back to the laboratory to reset the teeth. If no adjustments are needed, the wax try-in is sent back to the laboratory to be processed and finished. In the laboratory, the existing base and wax are discarded, and replaced by a tightly fitting plastic denture base.

During a fifth visit, the finished denture is then inserted into the mouth of the patient and adjusted as needed. The denture is also checked for occlusion and corrected, if necessary. As discussed above, it may generally take at least four or more visits of a patient until the finished dentures are finally inserted into the mouth of the patient. Thus, the multi-step process of preparing a set of dentures, requiring several iterations between the dentist and the dental laboratory is time-consuming, labor intensive and costly.

Moreover, difficulties exist in producing a good quality denture due to the great diversity in sizes and shapes of patients' mouths, and facial features requiring custom fabrication of each denture. Thus, standardization of prefabricated dentures is very difficult. Proposals to overcome the shortcomings of the conventional methods, such as multiple visits, intensive labor, and laboratory time needed for the fabrication of dentures, have had little success.

The shortcomings of prior proposals to overcome some of the difficulties in producing a conventional custom denture include: (1) Difficulty in collecting all necessary data to fabricate a high quality denture during one visit using the conventional method; (2) Difficulty in taking an impression and measuring jaw relations together in the conventional tray; (3) Expense, complexity and length of the procedure; (4) Skill level required; (5) Poor fit to the bite of an individual patient; (6) Excessive thickness or thinness of the denture base; (7) Use of articulated models, plaster and wax; (8) Poor fit to the tissue area of an individual patient; and (9) Poor functionality. Therefore, there is a need for a method and apparatus that will reduce the length of the procedure, and the number of times the patient visits the dentist for fabrication of a denture while providing a perfect fit of the denture to the patient.

SUMMARY OF THE INVENTION

The present invention overcomes all of the aforementioned shortcomings by providing a dental device that is convenient for a health professional to manipulate and software that allows accurate manufacturing of a complete denture without intensive manual labor. The present invention reduces the number of patient visits, cost and time conventionally required to produce a custom denture.

In accordance with one exemplary embodiment of the present invention, a dental impression tray assembly includes an upper (maxillary) tray and a lower (mandibular) tray operable with the upper tray, the lower tray including a first (anterior) piece and a pair of second (posterior) pieces detachably attachable to the first piece. The dental impression tray further includes an intra-oral tracer that is configured to be detachably coupled to the first piece of the lower tray and inserted into the mouth to be placed between the upper tray and the first piece of the lower tray and to measure a vertical dimension and a centric relation.

In accordance with another exemplary embodiment of the present invention, a method of obtaining a gum impression of a patient's mouth during a patient's single visit to a dentist using a dental impression tray assembly including a lower tray and an upper tray to fabricate a denture includes inserting the lower tray, including a first piece and a pair of second pieces and loaded with a polymer material, into the patient's mouth to obtain a first impression, inserting the upper tray, including a third piece and a fourth piece and loaded with the polymer material, into the patient's mouth to obtain a second impression, measuring jaw relations using the first piece of the lower tray, the intra-oral tracer, and the third piece of the upper tray, taking a bite registration by filling up a gap between the first piece and the third piece with a bite registration material, and removing the first piece, intra-oral tracer, and the third piece with the bite registration material from the patient's mouth.

These and other embodiments will also become readily apparent to those skilled in the art from the following detailed description of the embodiments having reference to the attached figures, the invention not being limited to any particular embodiment disclose.

BRIEF DESCRIPTION OF THE DRAWINGS

The above and other aspects, features, and advantages of the present invention will become more apparent upon consideration of the following description of preferred embodiments, taken in conjunction with the accompanying drawings.

DETAILED DESCRIPTION OF PREFERRED EMBODIMENTS

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts.

Figure 1A:
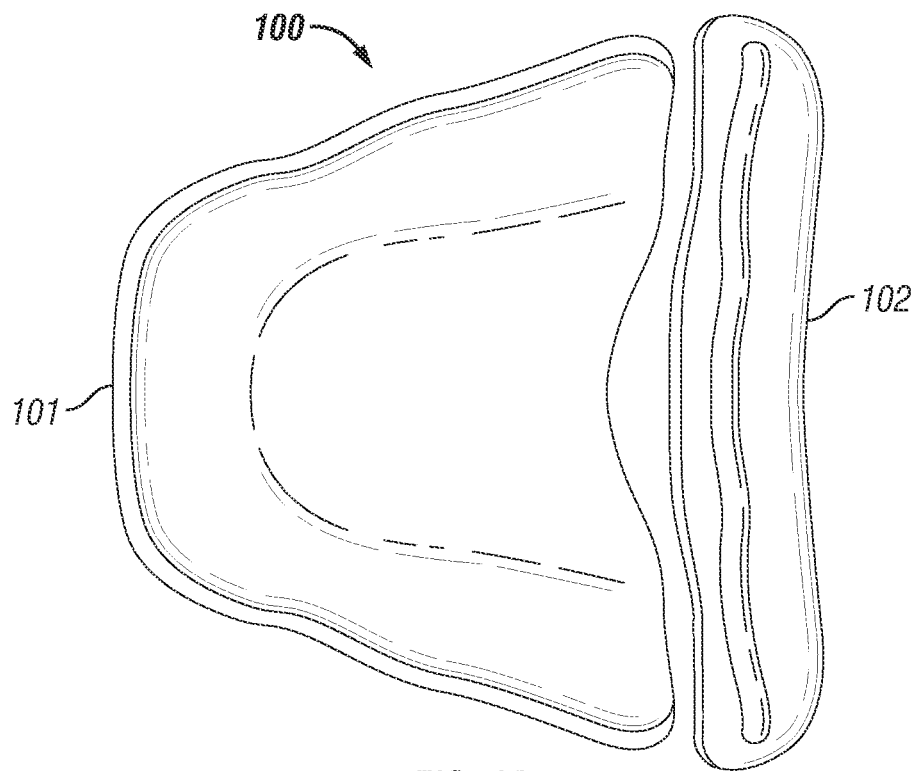
FIG. 1A is a top view of an upper tray according to an embodiment of the present invention, the upper tray comprising a first (center) piece and a second (outer) piece where the first piece and the second piece are separated.
Figure 1B:
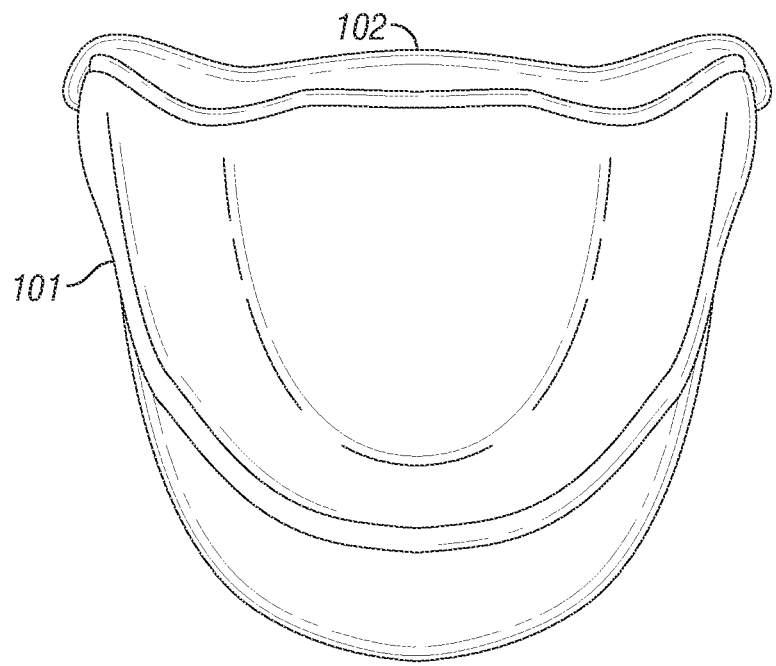
FIG. 1B is a top view of the upper tray where the first piece and the second piece are combined.
Figure 1C:
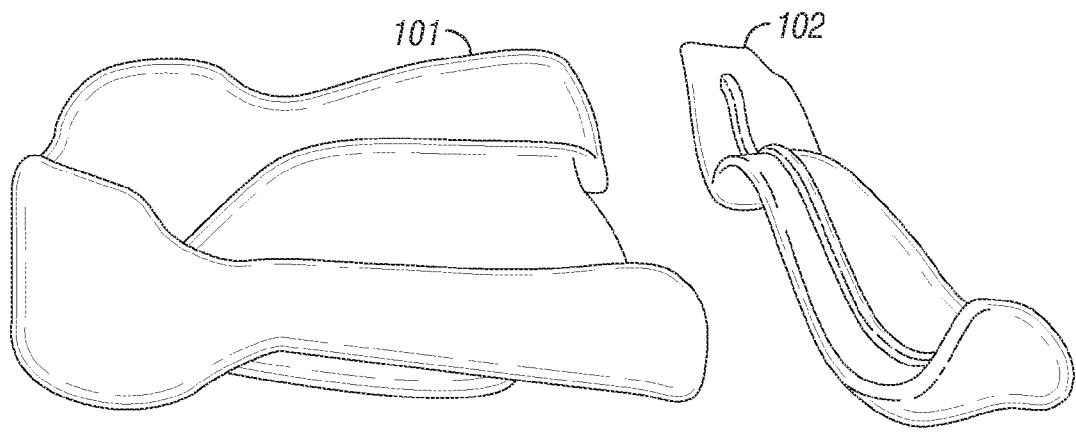
FIG. 1C is a disassembled perspective view of the upper tray.
Figure 1D:
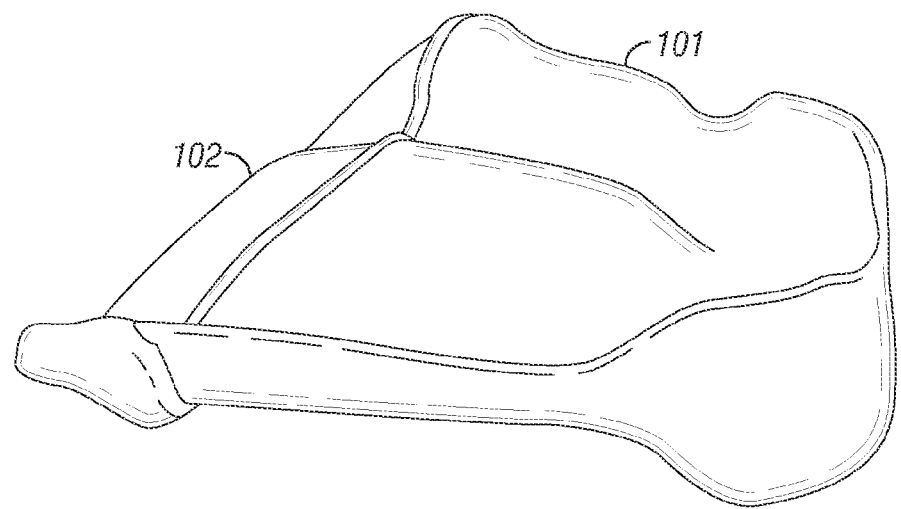
FIG. 1D is an assembled perspective view of the upper tray.
Figure 2A:
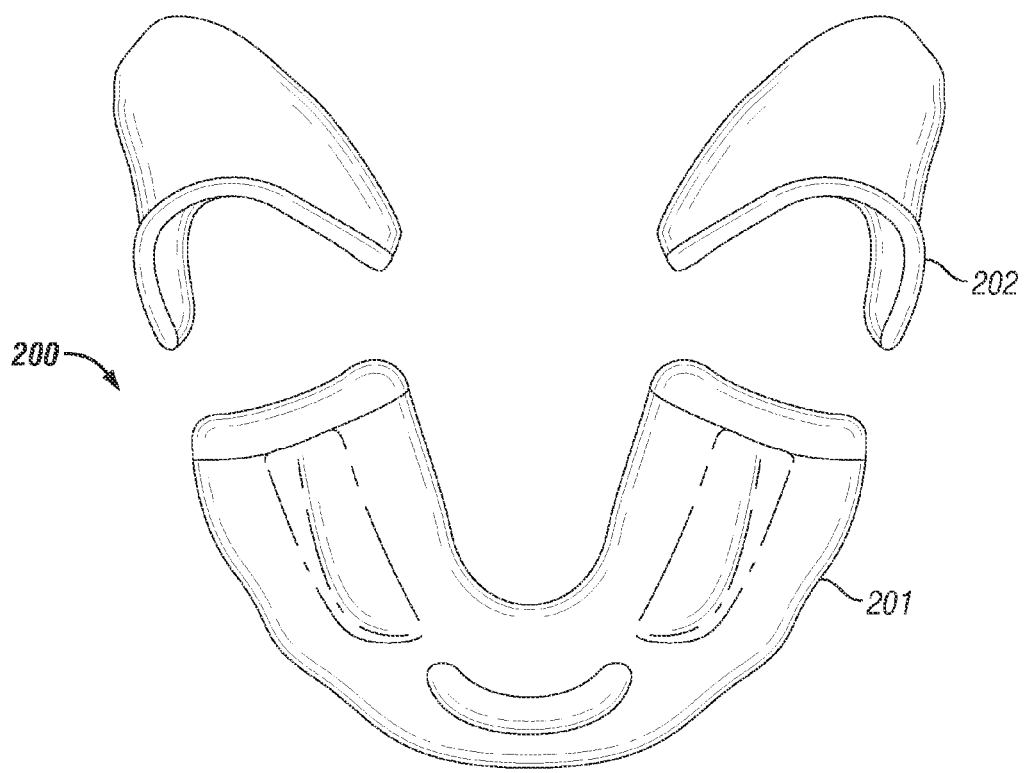
FIG. 2A is a top view of a lower tray according to an embodiment of the present invention, the lower tray comprising a third (center) piece and a pair of fourth (back) pieces where the third piece and the pair of fourth pieces are separated.
Figure 2B:
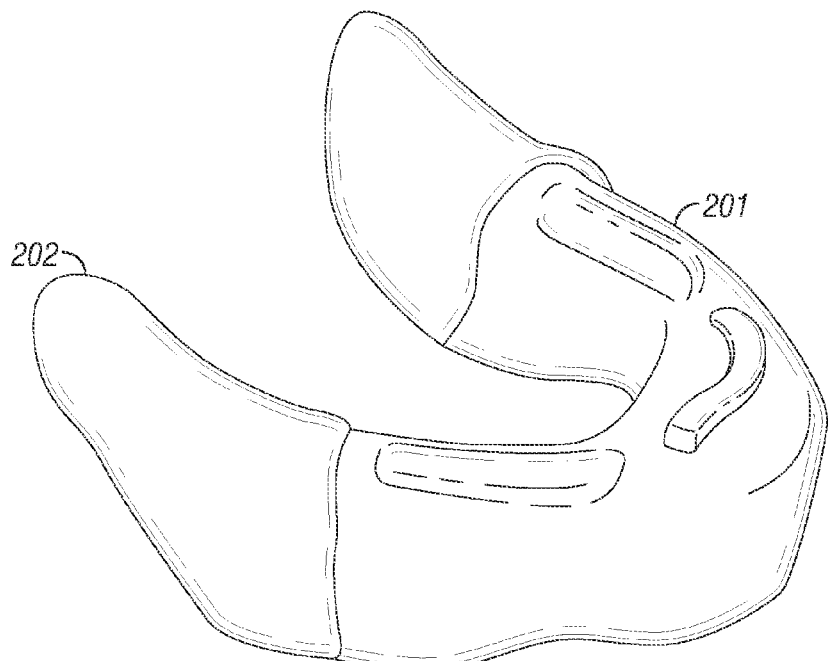
FIG. 2B is a perspective view of the lower tray in which the third piece and the pair of fourth pieces are assembled.
Figure 2C:
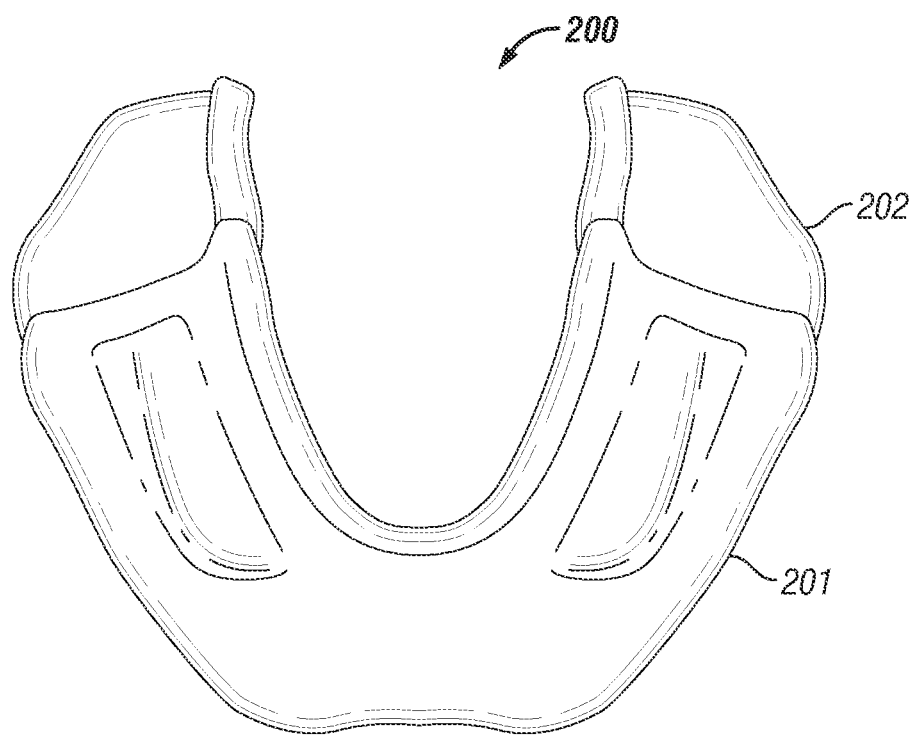
FIG. 2C is a bottom view of the lower tray in which the third piece and the pair of fourth pieces are assembled.

According to an embodiment of the present invention, the inventive set of trays, including an upper tray 100 and a lower tray 200, are capable of measuring jaw relations and taking a final impression in a single visit. The set of trays 100 and 200 may be made of plastic and may be available in various sizes to accommodate different sizes of jaws. The set of trays 100 and 200 may include a plurality of pieces or portions that can be assembled or disassembled. The upper tray 100 may be formed as a single piece rather than two pieces 101 and 102 as shown in FIGS. 1A-1D. The lower tray 200 comprises a plurality of pieces 201 and 202 as shown in FIGS. 2A-2B to be accommodated in a mouth of a patient.

The upper tray 100 and the lower tray 200, as shown in FIGS. 1A-1D and FIGS. 2A-2B, respectively, are used individually to take a maxillary (upper) impression and a mandibular (lower) impression, respectively. When the maxillary impression is taken using the upper tray 100, the upper tray 100 includes both the first piece 101 and the second piece 102. Further, when the mandibular impression is taken using the lower tray 200, the lower tray 200 includes both the third piece 201 and the pair of fourth pieces 202. For example, a polymer material, such as polyvinyl siloxane (PVS), is loaded on the first piece 101 and the second piece 102 of the upper tray 100, and the upper tray 100 retaining the polymer material is inserted into the mouth to obtain the maxillary impression of a patient's gum. Similarly, the polymer material is loaded on the third piece 201 and the pair of fourth pieces 202 of the lower tray 200, and the lower tray 200 retaining the polymer material is inserted into the mouth to obtain the mandibular impression of the patient's gum.

While the polymer material is still on the upper tray 100, the polymer material is cut, substantially along a single line or borderline where the first piece 101 and second piece 102 meet. For example, a surgical blade may be used to cut the polymer material on the upper tray 100. Once the polymer material on the upper tray 100 is cut completely, the first piece 101 and the second piece 102 containing the respective cut polymer material are separated carefully. Excess impression (polymer) material covering outer surfaces of the first piece 101 and the second piece 102 may be trimmed so that bite registration material can be seated. Similarly, the polymer material on the lower tray 200 is cut substantially along a single line between the third piece 201 and the pair of fourth pieces 202. Once the polymer material on the lower tray 200 is cut completely, the pair of fourth pieces 202 are separated from the third piece 201.

Figure 3A:
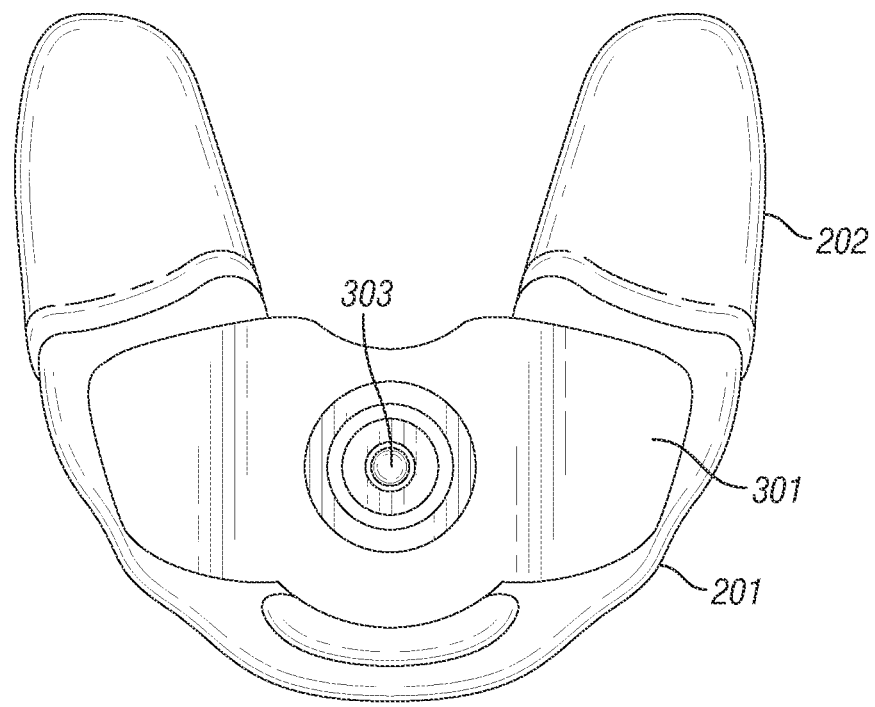
FIG. 3A is a top view of the assembled lower tray to which an intra-oral tracer is attached according to an embodiment of the present invention.
Figure 3B:
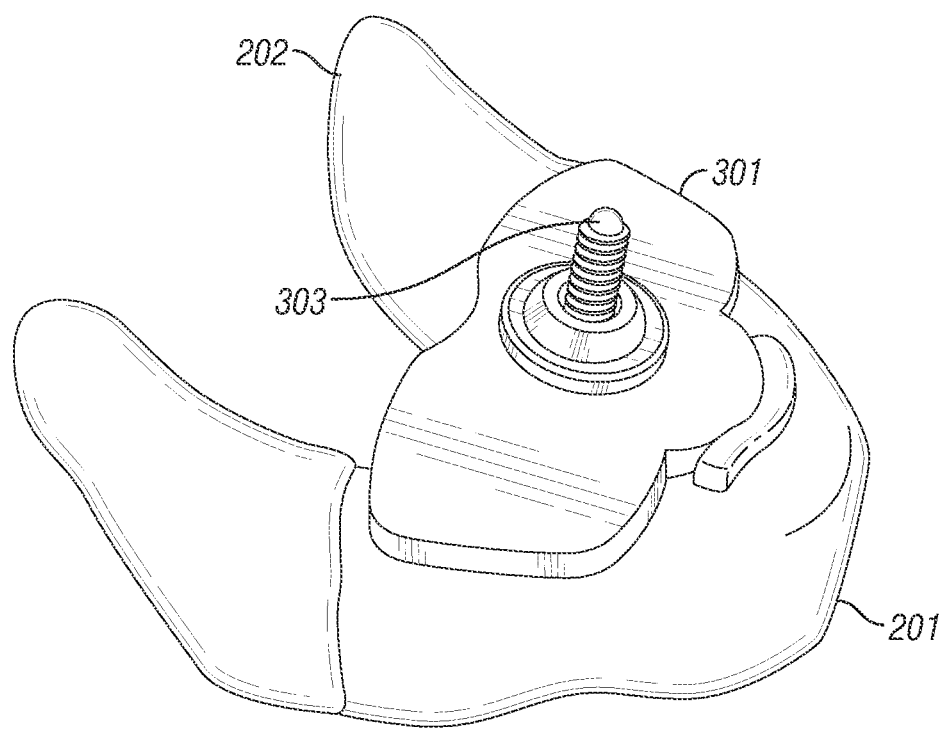
FIG. 3B is a perspective view of the assembled lower tray to which the intra-oral tracer is attached.
Figure 4:
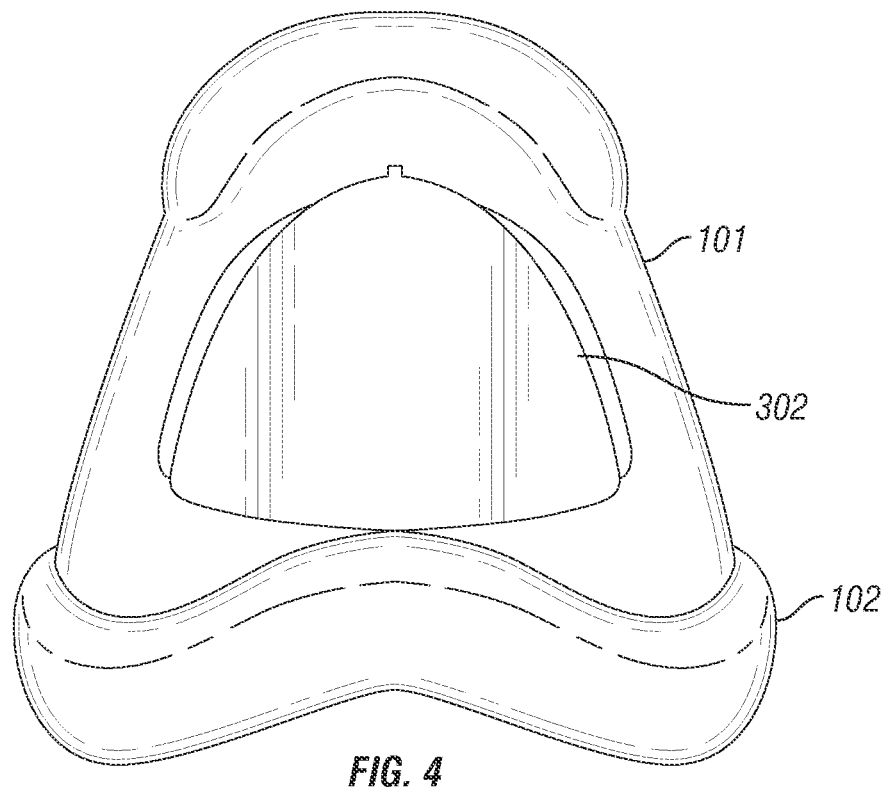
FIG. 4 is a bottom view of the assembled upper tray to which a cover to be contacted by the intra-oral tracer is attached.
Figure 5A:
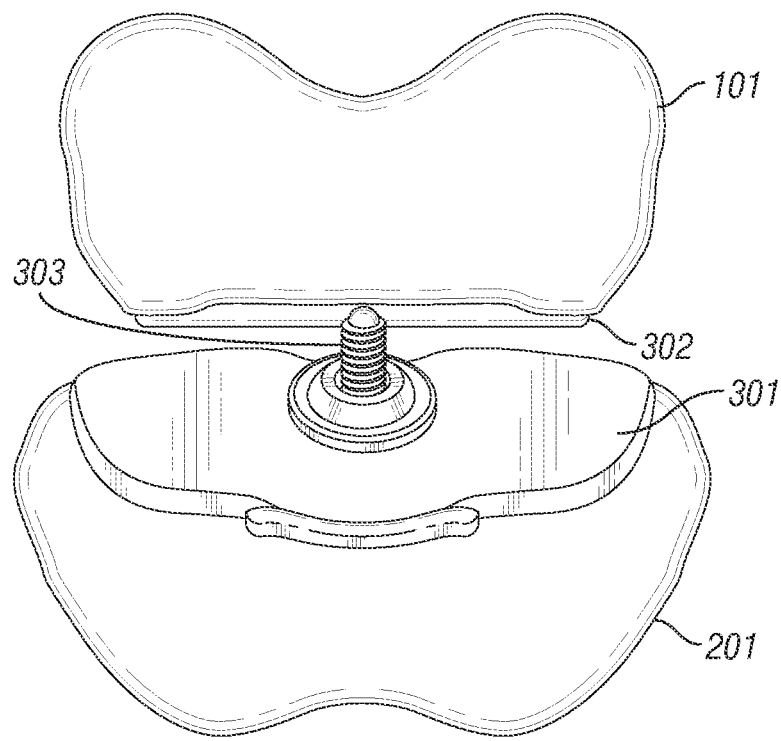
FIG. 5A is a frontal view of the first piece of the upper tray with the cover and the third piece of the lower tray with the intra-oral tracer, the intra-oral tracer contacting the cover.
Figure 5B:
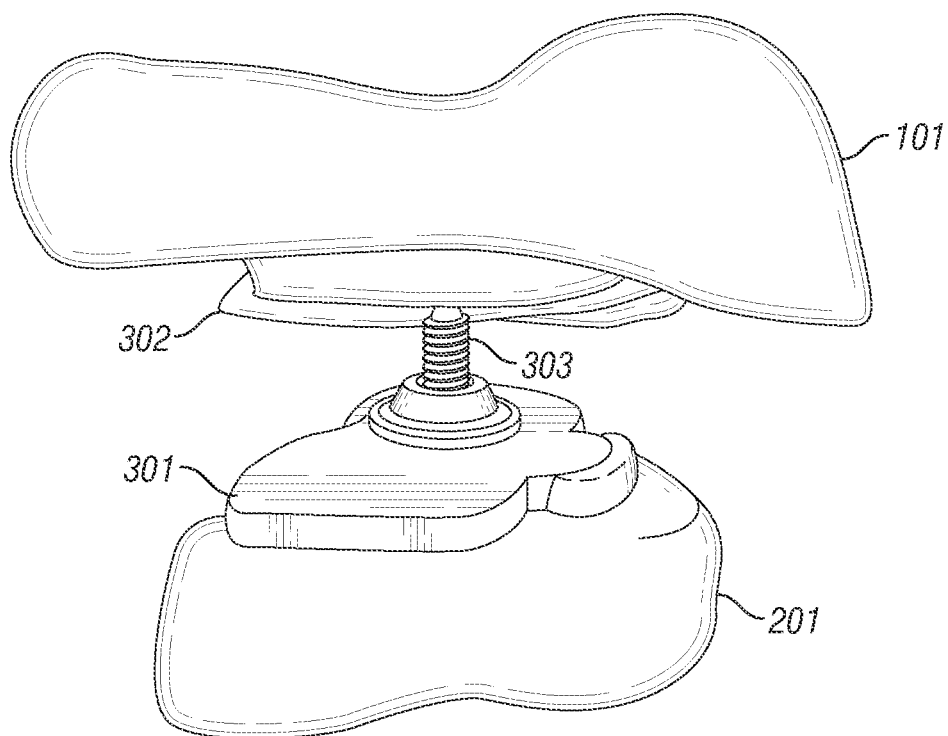
FIG. 5B is a side view of the first piece of the upper tray with the cover and the third piece of the lower tray with the intra-oral tracer, the intra-oral tracer contacting the cover.

Thereafter, the first piece 101 and the third piece 201 retaining the partial impression (polymer material) are inserted into the mouth together with an intra-oral tracer 301 placed between the first piece 101 and the third piece 201 as shown in FIGS. 5A and 5B. For example, the intra-oral tracer 301 may be inserted into the third piece 201 of the lower tray 200 configured to receive the intra-oral tracer 301, as shown in FIGS. 3A and 3B. Further, a cover 302 may be placed on a lower surface of the first piece 101 of the upper tray 100 as shown in FIG. 4. Alternatively, the upper tray 100 may not need a separate cover that needs to be manually placed because a portion to be covered by the cover 302 may be already covered by an integrally formed cover. The partial upper piece 100 and the partial lower piece 200, i.e., the first piece 101 and the third piece 201, respectively, and the intra-oral tracer 301, as shown in FIGS. 5A and 5B, are inserted into the mouth together to measure jaw relations such as a vertical dimension (VD) and a centric relation (CR). When the upper tray 100 and the lower tray 200 are inserted into the mouth together, the second piece 102 and the pair of fourth pieces 202 are not attached to the first piece 101 and the third piece 201, respectively. Jaw relations are measured by lowering or raising the screw 303 of the intra-oral tracer 301 in the mouth to contact the cover 302. Once the intra-oral tracer 301 is adjusted to be in a clinically acceptable position, a polymer material is filled in between the first piece 101 and the third piece 201 to obtain a bite registration. After the polymer material is filled to obtain the bite registration, the entire piece is removed from the patient's mouth.

In order to measure the jaw relation record, the mouth of the patient needs to be able to accommodate the trays when they are inserted into the mouth. However, if full-sized trays, such as conventional trays, are inserted into the mouth, it is practically impossible for the patient's mouth to accommodate the full-sized conventional trays because the end portions of the upper and lower trays contact each other at the posterior position of the mouth, thus becoming very bulky in the mouth. In order to solve this problem, the trays of the present invention have been sized to be accommodated in the mouth. For example, the dissembled trays, or a full sized upper tray and the dissembled lower tray, cover at least an anterior position of the mouth while not covering the entire region of the mouth. Therefore, according to the present example, jaw relations can be measured after obtaining the full impression of the patient's gum first using the full-sized upper tray 100 and the lower tray 200 individually, and then by cutting the obtained impression and separating the first piece 101 and the second piece 102 of the upper tray 100 and separating the third piece 201 and the pair of fourth pieces 202 of the lower tray 200.

The shapes of the trays have unique dimensions, the first piece 101 providing the position of the tray and the third piece 201 supporting the borders and capturing muscle movements. The first and third pieces 101 and 201 may have openings to retain the impression material.

According to another embodiment of the present invention, software is used to obtain a virtual model of the denture to be fabricated. From the scanned data of the PVS impression of the upper and lower trays 100 and 200, a three-dimensional (3-D) model is generated in a computer. The inventive software is used to fabricate dentures by taking the measurements of edentulous regions of the maxilla and mandible from the respective impressions. Further, information on the VD and CR obtained by using the inventive tray assembly is input into the software to create the dentures. The software synthesizes all the data and creates a 3-D model of the edentulous ridge and generates the placement of the teeth and gingival tissue. Included in the software are various sets of teeth types, varying based on shape, size and color. After selecting a desired tooth type, the software automatically generates a denture with the above discussed three reference points to correctly place the teeth. Furthermore, the software corrects any overlap of tooth structure that may arise from a discrepancy between the selected tooth type and the measurements entered from the impressions and gathered data. Once the virtual denture is created, the software will export the file to allow fabrication of the custom denture.

According to yet another embodiment of the present invention, the final denture is milled based on the above described information. Upon receiving the file of the virtual denture generated by the software, a machine will mill an acrylic block into the real denture. The milling denture comprises two different pieces. The first piece is on the teeth portion, and the second piece is on the gingival portion. Each piece is milled separately, and after milling, the two pieces are put together to form the denture.

Alternatively, the denture may be fabricated by rapid prototyping or a combination of the rapid prototyping and a conventional flasking technique. This allows different colors to be used to represent gingival and teeth colors in one operation, using the colors from the rapid prototyping, which are derived from the model.

The present disclosure relates to the art and science of dental prosthetics whereby dental professionals can produce a high quality complete denture at a substantially reduced cost, and in a reduced time, by using newly invented devices and software. It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A method of obtaining a gum impression of a patient's mouth and measuring jaw relations using a dental impression tray assembly comprising a lower tray and an upper tray to fabricate a denture, the upper tray comprising a first piece and a second piece and the lower tray comprising a third piece and a pair of fourth pieces, the method comprising:

loading a first impression material on the lower tray comprising the third piece and the pair of fourth pieces;

inserting the lower tray comprising the third piece and the pair of fourth pieces and loaded with the first impression material into the patient's mouth to take a lower impression;

taking out the lower tray from the patient's mouth and cutting the first impression material on the lower tray proximate to a borderline between the third piece and the pair of fourth pieces such that the taken lower impression is divided into a first impression corresponding to the third piece, a second impression corresponding to one of the pair of fourth pieces, and a third impression corresponding to the other one of the pair of fourth pieces;

separating the third piece from the pair of fourth pieces such that the first impression is retained on the separated third piece and the second impression and the third impression are retained on the separated pair of fourth pieces;

loading a second impression material on the upper tray comprising the first piece and the second piece;

inserting the upper tray comprising the first piece and the second piece and loaded with the second impression material into the patient's mouth to take an upper impression;

taking out the upper tray from the patient's mouth and cutting the second impression material on the upper tray proximate to a borderline between the first piece and the second piece such that the taken upper impression is divided into a fourth impression corresponding to the first piece, a fifth impression corresponding to the second piece;

separating the first piece from the second piece such that the fourth impression is retained on the separated first piece and the fifth impression is retained on the separated second piece;

attaching an intra-oral tracer to the separated third piece of the lower tray, the intra-oral tracer comprising an adjustable member that is inserted into a hole formed on the intra-oral tracer;

inserting the third piece to which the intra-oral tracer is attached and the separated first piece into the patient's mouth together to measure the jaw relations;

adjusting the adjusting member by raising or lowering the adjusting member to determine a vertical dimension and to adjust a size of a gap between the third piece and the first piece;

filling the gap with a bite registration material; and removing the entire piece including the third piece, first piece, and intra-oral tracer from the patient's mouth when the bite registration material is set at the gap.

2. The method of claim 1, further comprising:

scanning the gum impression including the upper impression and the lower impression; and fabricating the denture using software processed in a computer based upon a scanned image of the gum impression.

3. The method of claim 2, further comprising:

generating a virtual model of the denture using the software; and virtually combining imported three-dimensional images of the patient's soft tissue of the mouth and new three-dimensional images that represent teeth.

4. The method of claim 3, further comprising:

importing and displaying multiple three-dimensional images using the software;

manipulating the three-dimensional images to locate them to a proper relative location in the patient's mouth; and selecting desired types of teeth and aligning the teeth to form a proper arch with a proper occlusal relationship according to anatomical information determined from the three-dimensional images of the patient's soft tissue of the mouth.

5. The method of claim 4, further comprising:

further manipulating the combined three-dimensional images by building up gum tissue where no tissue exists currently and by truncating the teeth to fit into existing gum.

6. The method of claim 1, wherein the third piece of the lower tray is sized to cover an anterior portion of the patient's lower gum and the pair of fourth pieces are sized to cover distal portions or the rest of the lower gum when attached to the third piece such that a size of the lower tray including the third piece and the pair of fourth pieces is fixed.

7. The method of claim 1, wherein the pair of fourth pieces are configured to be detached from the third piece after taking the lower impression and the second piece is configured to be detached from the first piece after taking the upper impression.

8. The method of claim 1, wherein the third piece of the lower tray with the intra-oral tracer attached and the first piece of the upper tray are configured to be inserted together into the patient's mouth to determine the jaw relations comprising the vertical dimension and a centric relation.

9. The method of claim 1, wherein the third piece, which is substantially U-shaped, is sized and configured to fit over at least an anterior portion of lower gum of the patient's mouth.

10. The method of claim 9, wherein each of the pair of fourth pieces, which is configured to be detachably coupled to each of two end portions of the substantially U-shaped third piece, is sized and configured to fit over a posterior portion of the lower gum when the pair of fourth pieces are coupled to the third piece.

11. The method of claim 1, wherein the first piece is sized and configured to fit over at least an anterior portion of upper gum of the patient's mouth.

12. The method of claim 11, wherein the second piece, which is detachably coupled to the first piece, is sized and configured to fit over a posterior portion of the upper gum.

13. The method of claim 1, wherein the intra-oral tracer is configured to be detachably coupled to the third piece of the lower tray, the intra-oral tracer comprising an connection portion that is inserted into a receiving portion of the third piece.

14. The method of claim 13, wherein the intra-oral tracer is coupled to the third piece such that an open space of the U-shaped area is substantially covered by the intra-oral tracer.

15. The method of claim 1, wherein a size of the lower tray including the third piece and the pair of fourth pieces and a size of the upper tray including the first piece and the second piece are fixed.

16. The method of claim 1, wherein the third piece of the lower tray with the intra-oral tray attached and the first piece of the upper tray are sized to be inserted together into the mouth to determine the jaw relations.

* * * * *